United States Patent

Dirlam et al.

[11] Patent Number: 5,891,727
[45] Date of Patent: Apr. 6, 1999

[54] ACIDIC POLYCYCLIC ETHER USEFUL AS AN ANTICOCCIDIAL AGENT AND AS A GROWTH PROMOTANT

[75] Inventors: John P. Dirlam, Gales Ferry; Walter P. Cullen, East Lyme, both of Conn.; Hiroshi Maeda, Chita-Gun; Junsuke Tone, Chita, both of Japan

[73] Assignee: Pfizer Inc., New York, N.Y.

[21] Appl. No.: 849,553

[22] Filed: Mar. 11, 1992

Related U.S. Application Data

[63] Continuation of Ser. No. 487,947, Apr. 16, 1990, Pat. No. 5,147,858.

[51] Int. Cl.$^6$ ........................................................ C12N 1/00
[52] U.S. Cl. ................................ 435/825; 435/2; 514/25; 514/27; 536/16.8; 536/18.1
[58] Field of Search .................................. 536/16.8, 18.1; 514/25, 27; 435/72, 825

[56] References Cited

U.S. PATENT DOCUMENTS

| | | | |
|---|---|---|---|
| 4,148,882 | 4/1979 | Celmer et al. | 424/122 |
| 4,195,079 | 3/1980 | Celmer et al. | 424/122 |
| 4,582,822 | 4/1986 | Hamill et al. | 514/25 |
| 4,746,650 | 5/1988 | Cullen et al. | 514/27 |

OTHER PUBLICATIONS

Ruddock et al, Chemical Abstracts, vol. 104, 1986 No. 166, 918 n.

*Primary Examiner*—Elli Peselev
*Attorney, Agent, or Firm*—Peter C. Richardson; Paul H. Ginsburg; Jolene W. Appleman

[57] ABSTRACT

An acidic polycyclic ether antibiotic, having structure established by X-ray crystallography, is formed by fermentation of a novel microorganism, Actinomadura sp. ATCC 53676. This novel antibiotic is useful as an anticoccidial in chickens and as a growth promotant in cattle and swine.

2 Claims, No Drawings

ACIDIC POLYCYCLIC ETHER USEFUL AS AN ANTICOCCIDIAL AGENT AND AS A GROWTH PROMOTANT

This is a continuation, of application Ser. No. 07/487,947 filed on Apr. 16, 1990 now U.S. Pat. No. 5,147,858.

BACKGROUND OF THE INVENTION

The present invention concerns a new acidic polycyclic ether antibiotic having the absolute stereo-chemical formula

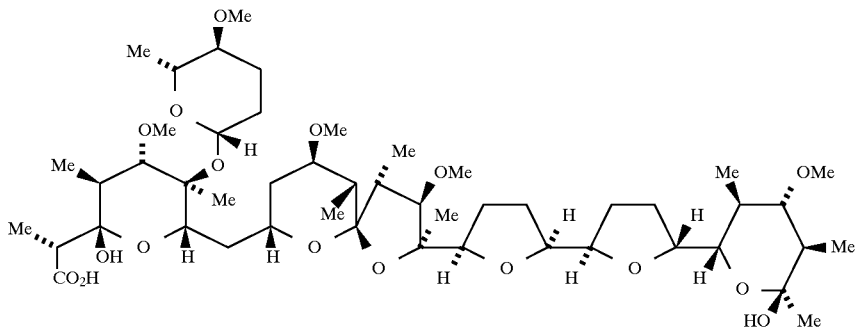

wherein Me=$CH_3$; pharmaceutically acceptable cationic salts thereof; nutrient feed compositions comprising said antibiotic for poultry, cattle or swine; its use as an anticoccidial agent in poultry, or as a growth promotant in cattle or swine; a fermentation method for its preparation; and the Actinomadura sp. microorganism which produces said antibiotic in said fermentation method.

The compound (I) is a new member of the acidic polycyclic ether group of antibiotics. This family includes such well known agents as monensin (The Merck Index, 10th Ed., Merck and Co., Inc., Rahway, N.J., 1983, monograph no. 6100), nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 177–223 (1977). These compounds are generally known as coccidiostats and/or as feed additive-growth promotants.

SUMMARY OF THE INVENTION

A culture of Actinomadura sp., ATCC 53676, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Actinomadura sp. ATCC 53676 in an aqueous nutrient medium comprising an assimilable source of carbon and nitrogen until a recoverable amount of said compound of the formula (I) is formed, preferably under submerged aerobic conditions. For use as an anticoccidial agent and/or a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylene-diamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of Actinomadura sp. ATCC 53676, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Actinomadura sp., and has been deposited in The American Type Culture Collection, Rockville, Maryland as the type culture under their accession number ATCC 53676. Permanency of the deposit of this culture at The American Type Culture Collection at Rockville, Maryland and ready accessibility thereto by the public are afforded throughout the effective life of the patent in the event the patent is granted. Access to the culture is available during pendency of the application under 37 CFR 1.14 and 35 USC 122. All restrictions on the availability to the public of the culture deposited will be irrevocably removed upon granting of the patent.

This novel culture was derived from a soil sample collected in Hongo Town, Toyama City, Toyama Prefecture, Japan, and identified in the culture collection of Pfizer Inc. as N742-34. Its description and classification were provided by Dr. L. H. Huang. This culture was found to produce narrow dimensions of the hyphae of the actinomycetes, an aerial mycelium upon which spore chains are produced, and an unfragmented substrate mycelium. The results of the whole cell analyses further indicate that it belongs to the genus Actinomadura.

A slant culture of the microorganism was planted into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the result read at varying times, but most commonly at fourteen days. The colors were described in common terminology, but exact colors were determined by comparisons with color chips from The Color Harmony Manual, fourth edition. The methods of whole-cell amino acid and sugar analyses are those described in Becker et al., Appl. Microbiol., vol. 12, pp. 421–423 (1964), and in Staneck et al., Appl Microbiol., vol. 28, pp. 226–231 (1974) and Lechevalier, J. Lab. Clin. Med., Vol. 71, pp. 934–944 (1968), respectively. For purposes of comparison, Actinomadura citrea ATCC 27887, A. cremea ATCC 33577 and A. macra ATCC 31286 were used.

The culture was identified as follows:

Yeast Extract-Malt Extract Agar (ISP #2 medium, Difco) —Growth good, grayish yellow, gray to grayish black (2 gc, 2 ie, 2 li, 2 nl); raised, wrinkled; aerial mycelium sparse, white to pale gray (near gray series 3 dc); reverse yellowish gray, gray to grayish black (2 de, 2 li, 2 nl); soluble pigment yellowish (2 lc).

Oatmeal Agar (ISP #3 medium, Difco)—Growth moderate, pale greenish yellow (1½ ca, 1 ca, 1 ea); slightly raised, smooth, no aerial mycelium; reverse same as surface; soluble pigment none to cream (1½ ca).

Inorganic Salts-Starch Agar (ISP #4 medium, Difco)— Growth poor, pale green-yellow (1½ ea, 1 ea), thin, smooth, aerial mycelium none or sparse, colorless; reverse same as surface; no soluble pigment.

Glycerol-Asparagine Agar (ISP #5 medium, Difco)— Growth poor to moderate, pale pink (3 ca); thin to slightly raised; aerial mycelium none to sparse, colorless; reverse pale pink (3 ca); no soluble pigment.

Czapek-Sucrose Agar (Waksman, "The Actinomycetes", v. 2, medium #1, p. 328, 1961)—Growth moderate, cream (1½ ca); slightly raised, smooth; aerial mycelium none to sparse, colorless; reverse colorless to cream (1½ ca); no soluble pigment.

Glucose-Asparagine Agar (ibid., medium #2)—Growth moderate; off-white, cream, yellowish to yellowish brown (2 ca, 2 lc, 3 lc); slightly raised, smooth, aerial mycelium off-white; reverse yellowish to yellowish brown (2 ga, 3 lc); soluble pigment pale yellowish (2 ea).

Gordon and Smith's Tyrosine Agar (Gordon and Smith, J. Bacteriol., 69:147–150, 1955)—Growth moderate, brown (3 le, 3 lg); thin but may be raised toward end of streak, smooth, no aerial mycelium, reverse brown (3 le); soluble pigment yellowish (2 lc).

Calcium Malate Agar (Waksman, Bacteriol. Rev. 21, 1–29, 1957)—No growth.

Casein Agar (Gordon and Smith, ibid.)—Growth moderate, yellowish brown to brown (3 ic, 3 le); slightly raised, smooth, no aerial mycelium; reverse yellowish to yellowish brown (2 nc, 3 lc); soluble pigment yellowish brown (3 lc).

Bennett's Agar (Waksman, loc. cit., medium #30, p. 331)—Growth good to excellent, yellowish brown to brown (3 ic, 4 lg, 3 ni); raised, wrinkled; aerial mycelium, white to off-white, produced toward the margin; reverse dark brown (3 li, 3 ni); soluble pigment yellowish (2 lc).

Emerson's Agar (ibid., medium #28, p. 331)—Growth good, yellowish gray (2 ie, 2 lg, 2 ni), raised, wrinkled; aerial mycelium pale gray (near gray series 3 dc); reverse yellowish gray to greenish gray (2 ng, 1½ ng); soluble pigment yellowish brown (3 ne).

Nutrient Agar (ibid., medium #14, p. 330)—Growth poor to moderate, yellowish brown to brown (3 lc, 3 ic, 3 le), slightly raised, smooth but granular in some areas, confluent or appearing as isolated colonies; no aerial mycelium; reverse yellowish brown (3 lc); no soluble pigment.

Gelatin Agar (Gordon and Mihm, J. Bacteriol. 73, 15–27, 1957)—Growth moderate, brown (3 nc, 3 le); moderately raised, smooth but wrinkled toward end of streak, no aerial mycelium; reverse brown (3 le); no soluble pigment.

Starch Agar (ibid.)—Growth moderate, brown (3 ne); moderately raised, smooth but wrinkled toward edge; aerial mycelium none to sparse, colorless; reverse brown (3 ie); no soluble pigment.

Potato Carrot Agar (Lechevalier, Lab. Clin. Med., 71, 934–944, 1968, but use only 30 g. potatoes, 2.5 g. carrots and 20 g. agar)—Growth poor to moderate, cream (1½ ca); thin to slightly raised, smooth, aerial mycelium sparse, colorless; reverse colorless to cream (1½ ca); no soluble pigment.

Tap Water Agar (2%)—Growth poor, colorless to cream (2 ca); thin, smooth, aerial mycelium sparse, colorless; reverse colorless; no soluble pigment.

Gauze's Mineral Medium 1 (Gauze et al., Problems in the Classification of Antagonistic Actinomycetes, English Ed., p. 13, 1957)—Growth moderate, yellowish green (1 ic), thin, smooth; aerial mycelium sparse, colorless; reverse pale yellowish green to yellowish green (1 ea, 1 ic); soluble pigment pale cream (1½ ca).

Gauze's Mineral Medium 2 (ibid.)—Growth good, yellowish brown to pink (3 gc, 3 ic, 5 gc), raised, wrinkled, with white aerial mycelium; reverse yellowish brown to orange brown (3 gc, 4 lc); no soluble pigment.

Morphological Properties—The morphological properties were observed once a week for up to seven weeks. The culture did not produce spores on any media except for inorganic salts-starch agar. After seven weeks of incubation on this medium, a few small patches of spore chains were produced. They were short with 3 to 9 spores per spore chain and were straight, flexuous, curved to hooked. The spores were globose, oval to elliptical and measured 0.9–1.3 $\mu$m diam. or 1.0–1.6×0.8–1.1 $\mu$m. They were warty as revealed by scanning electron microscopy. In addition to the spores, the culture also produced brown to dark brown hyphal masses on glucose-asparagine agar, Bennett's agar, yeast extract-malt extract agar, inorganic salts-starch agar, and glycerol-asparagine agar. They were tightly interwoven structures which were globose, subglobose, elliptical, elongated or irregularly shaped, and measured 5–25 $\mu$m diam. or 8–25×7–20 $\mu$m.

Biochemical Properties—Melanin not produced; hydrogen sulfide not produced; gelatin liquefied; starch hydrolyzed; nitrate reduced to nitrite in dextrose nitrate broth, but not in organic nitrate broth; no growth and no decomposition on either Jensen's or Levine and Schoenlein's cellulose broth; coagulation and clearing on milk; casein digestion positive; tyrosine digestion positive. Carbohydrate utilization: glucose, rhamnose, sucrose, starch and trehalose utilized; arabinose, fructose, inositol, mannitol, raffinose, xylose, adonitol, cellobiose, dulcitol, erythritol, galactose, glycerol, lactose, maltose, mannose, melezitose, melibiose, alpha-methyl-D-glucoside, ribose, salicin, sorbitol and sorbose not utilized.

The other positive tests included utilization of acetate, propionate and pyruvate. The following tests were negative: decomposition of adenine, xanthine, hypoxanthine, and urease; hydrolysis of esculin and hippurate; and resistance to lysozyme.

| Temperature Relations — | | | |
|---|---|---|---|
| 21° C. | 28° C. | 37° C. | 45° C. |
| Moderate Growth | Good Growth | Good Growth | No Growth |

Whole-Cell Analyses—The whole-cell hydrolysates contained meso-diaminopimelic acid, glucose, galactose, madurose and ribose.

The culture N742-34 is characterized by the white to pale gray aerial mycelium; the green-yellow, yellow-brown to brown substrate mycelium; the short straight to flexuous spore chains; and the spores with a warty surface. The presence in the whole-cell hydrolysates of meso-diaminopimelic acid and madurose further indicates its belonging in the genus Actinomadura.

Among the more than forty species of Actinomadura, five resemble culture N742-34 in morphological and/or biochemical properties: *A. citrea, A. cremea, A. flava, A. livida,* and *A. macra*. Both *A. citrea* and *A. flava* produce a lemon-yellow substrate mycelium, as does culture N742-34. *A. flava* produces long spore chains and spores with a smooth surface whereas culture N742-34 forms short spore chains and spores with a warty surface. Unlike culture N742-34, *A. citrea* utilizes arabinose, xylose, mannitol and fructose.

*A. livida* forms spore chains in the form of hooks or spirals with a single turn, whereas culture N742-34 forms straight or flexuous spore chains. On oatmeal agar and Gauze #1 mineral medium, *A. livida* forms a pale violet soluble pigment, but culture N742-34 forms a cream soluble pigment.

*A. cremea* differs from culture N742-34 in positive utilization of arabinose, fructose, mannitol, xylose, adonitol, glycerol, lactate and succinate; negative utilization of sucrose and starch; and decomposition of esculin.

*A. macra* is closely similar to culture N742-34 in most of the biochemical properties. A few differences were noted. Unlike the former, the latter utilizes rhamnose and starch, hydrolyzes starch, coagulates milk, and decomposes casein. In addition, culture N742-34 produces mostly a yellow-green, yellow-brown or brown substrate mycelium and spores with a warty surface; whereas *A. macra* produces mostly a cream or gray substrate mycelium and spores with a smooth surface.

On the basis of the above, culture N742-34 is considered as a member of the genus Actinomadura and designated Actinomadura sp. It is the type of strain of Actinomadura sp. and has been deposited at the American Type Culture Collection under the assession number 53676.

The antibiotic compound (I) of the present invention is readily produced by the Actinomadura culture by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substance such as grain solubles, fish meal, cotton seed meal; mineral salts containing trace elements such as iron, cobalt, copper, zinc, etc. and calcium carbonate or phosphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Actinomadura sp. ATCC 53676. The resulting vegetative cells are in turn used to inoculate shake flasks or inoculum tanks, also containing suitable growth media. Alternatively, the inoculum tanks are inoculated from the shake flasks. Following a suitable growth period (e.g., 120–196 hours), the fermentor, also containing suitable growth media, is inoculated with vegetative broth from the shake flasks or inoculum tanks. Upon completion of growth (e.g., 120–196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and an inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as well as activity against *Treponema hyodysenteriae*, as illustrated in Table (I).

TABLE I

IN VITRO ANTIBACTERIAL ACTIVITY OF THE COMPOUND OF THE FORMULA (I)

| Organism | Strain No. | MIC, mcg/ml |
|---|---|---|
| *Clostridium perfringens* | 10A006 | 0.39 |
| | 10A009 | <0.20 |
| *Actinomyces pyogenes* | 14D002 | <0.20 |
| | 14D008 | <0.20 |

TABLE I-continued

IN VITRO ANTIBACTERIAL ACTIVITY OF THE
COMPOUND OF THE FORMULA (I)

| Organism | Strain No. | MIC, mcg/ml |
|---|---|---|
| Treponema hyodysenteriae | 14D011 | <0.20 |
| | 94A001 | <0.20 |
| | 94A002 | <0.20 |
| | 94A007 | <0.20 |

Efficacy data for the compound of the formula (I) and its salts against coccidial infections in chickens is obtained by the following method. Groups of 3–5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3–5 ten-day old chicks are fed a similar mash diet without compound (I) or its salts. They are also infected after 24 hours and serve as infected controls. Yet another group of 3–5 ten-day old chicks are fed the same mash diet without antibiotic and are not infected with coccidia. These served as normal controls. The results of treatment are evaluated after five days in the case of E. acervulina, and six days for all other challenges.

The criteria used to measure anticoccidial activity consists of lesion scores of 0 to 4 for E. tenella after J. E. Lynch, "A New Method of the Primary Evaluation of Anticoccidial Activity", Am. J. Vet. Res., 22, 324–326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", Exp. Parasit., 28, 30–36, 1970. Activity is measured by dividing the lesion score of each treated group by the lesion score of the infected control. In this test, the compound (I) and its cationic salts exhibit excellent activity against Eimeria tenella, E. acervulina, E. maxima, E. brunetti and E. necatrix infections in poultry when incorporated into the mash diet of chickens at levels of about 2.5 to 50 ppm.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude form such as wet or dry mycelium or dried whole broth. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to product a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 2.5 to 50 ppm, preferably in the range of about 2.5 to 12.5 ppm. When administered in drinking water, the level which will be that which will provide the same daily dose of medication factored by the weight ratio of the average daily consumption of feed to the average daily consumption of water.

The activity of the compound of the formula (I) and its salts in promotion growth and/or increasing the efficiency of food utilization in swine or cattle can be measured directly by feeding test groups of animals various levels of the compound (I) or a salt in feed. However, a more convenient technique is described in British Patent Specification No. 1,197,826, which details an in vitro rumen method for the evaluation of feeds. The changes occurring in feed, brought about by microorganisms, are thereby readily measured with great accuracy. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the micro-organisms. An increase in the propionic acid content of the rumen fluid indicates that a desirable response to overall ruminant performance has been brought about by the growth promotant in the feed composition. The change in propionic acid content is expressed as percent of the propionic acid content found in the control rumen fluid. Long term in vivo feeding studies have shown a reliable correlation between propionic acid increase in the rumen fluid and improved animal performance, whether ruminant (e.g. cattle, sheep) or monogastric (e.g. swine).

In detail, rumen fluid is collected from a fistulated cow which is fed on a commercial fattening ration plus hay. The rumen fluid is immediately filtered through cheese cloth, and 10 ml. added to a 50 ml. conical flask containing 400 mg. of standard substrate (68% corn starch+17% cellulose+15% extracted soybean meal), 10 ml. of a pH 6.8 buffer and the test compound. The flasks are gassed with oxygen free nitrogen for about two minutes, and incubated in a shaking water bath at 39° C. for about 16 hours. All tests are conducted in triplicate. After incubation, 5 ml. of the sample is mixed with 1 ml. of 25% meta-phosphoric acid. After 10 minutes 0.25 ml. of formic acid is added and the mixture centrifuged at 1500 rpm for 10 minutes. Samples are then analyzed by gas-liquid chromatography by the method of D. W. Kellogg, *J. Dairy Science*, 52, 1690, 1969. Peak heights for acetic, propionic and butyric acids are determined for samples from untreated and treated incubation flasks.

When tested by this in vitro procedure, the compound of the formula (I) at a level of 10 micrograms per milliliter gave rise to an increase of about 97% in the production of propionic acid over that produced in the control solution without added compound (I).

For use in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of about 0.25 to 50 ppm. In ruminants the compound of the formula (I) can also be orally administered in the form of a bolus which is retained in the rumenoreticular sac, releasing the therapeutic agent at a substantially constant rate over a prolonged period of time, e.g., 4–8 weeks, providing a dose equivalent to that of the above daily dose in feed, i.e.:

$$\left( \begin{array}{c} \text{(average daily dose} \\ \text{in milligrams} \end{array} \right) = \left( \begin{array}{c} 0.25 \text{ to } 50 \\ \text{ppm} \end{array} \right) \times \left( \begin{array}{c} \text{average daily feed} \\ \text{consumption in Kg} \end{array} \right).$$

Exemplary of such a controlled release bolus is that of Cardinal, U.S. Pat. No. 4,601,893.

The present invention is illustrated by the following examples. However, it should be understood that the invention is not limited to the specific details of these examples.

EXAMPLE 1

Fermentation of Actinomadura sp. ATCC 53676

The Actinomadrua sp. was initially grown by inoculating solid media on slants or Roux bottles with the ATCC 53676 culture, using ATCC medium No. 172, prepared and having composition as follows.

|  | Grams/liter |
|---|---|
| Glucose | 10 |
| Soluble Starch | 20 |
| Yeast Extract | 5 |
| Casein Enzymatic Hydrolysate | 1 |
| Calcium Carbonate | 1 |
| Distilled Water to 1000 ml; | 20 |
| pH to 7.0 with KOH; Add Agar | |

Meanwhile, shake flasks were prepared using one or the other of the following media:

| C' | Grams/liter | JDYTT | Grams/liter |
|---|---|---|---|
| Cerelose | 10 | Cerelose | 10 |
| Soy Flour | 10 | Corn Starch | 5 |
| Corn Ferm Prod | 5 | Corn Steep Liquor | 5 |
| Corn Starch | 10 | Casein Enzymatic | 5 |
| Sodium Chloride | 5 | Hydrolysate | |
| Cobalt Chloride | 0.002 | Cobalt Chloride | 0.002 |
| Calcium Carbonate | 1 | Calcium Carbonate | 3 |

One hundred ml of medium was distributed into 300 ml shake flasks and sterilized at 120° C. and 15 p.s.i. for 30 minutes. After cooling, the medium was inoculated with a vegetative cell suspension scraped from the above Actinomadura sp. slant culture. The flasks were shaken at 28° C. on a shaker having a displacement of 1.5 to 2.5 inches and 150 to 200 cycles per minute (CPM) for five to seven days.

Meanwhile, 5 liter fermentation vessels were prepared containing 3 liters of one of the following media:

| C' | Grams/liter | JDY TT | Grams/liter |
|---|---|---|---|
| Cerelose | 10 | Cerelose | 10 |
| Corn Starch | 10 | Corn Starch | 5 |
| Soybean Flour | 10 | Corn Steep Liquor | 5 |
| Corn Ferm Solids | 5 | Cobalt Chloride | 0.002 |
| Sodium Chloride | 5 | Casein Enzymatic | 5 |
| Cobalt Chloride | 0.002 | Hydrolysate | |
| Calcium Carbonate | 1 | Calcium Carbonate | 3 |
| or | | | |

| UK1-2 | Grams/liter |
|---|---|
| Cerelose | 45 |
| Soy Flour | 10 |
| Corn Steep Liquor | 10 |
| Cobalt Chloride | 0.002 |
| Magnesium Sulfate | 0.10 |
| Calcium Carbonate | 3 |
| Manganese Sulfate | 0.10 |
| Ferric Sulfate | 0.10 |

An antifoaming agent (polypropyleneglycol, P2000, containing 10% ethylene oxide by weight, 1 ml) was added, and the vessels were sealed and sterilized at 120° C. and 15 p.s.i. for 45 minutes. The vessels were then inoculated with one shake flask (ca 3% inoculum), fermented for 120 to 168 hours at 30° C., stirring at 1700 revolutions per minute (RPM) with an air rate of one volume of air per volume of liquid per minute.

When the fermentation was completed (based on an antibiotic disc assay versus *B. subtilis* ATCC 6633) the fermenters were stopped and filtered at the natural pH with the aid of a diatomaceous earth. The filter cake was slurried in methanol, concentrated in vacuo, diluted with 2–3 volumes of water then extracted 2× with ⅓ to ½ volume of either methylisobutyl ketone or n-butanol. The solvent layer was separated from the aqueous phase by aspiration or centrifugation, sparkled and concentrated in vacuo to yield the antibiotic of the formula (I) in crude form as a viscous oil.

The bioactivity of the broth and subsequent recovery streams can be followed by using a sensitive strain of *Bacillus subtilis* ATCC 6633 or *Staphylococcus aureus* ATCC 6538. The components in the broth and recovery streams can be visualized by using Analtech silica gel GF plates employing ethyl acetate as eluant. The developed plates are sprayed with vanillin reagent (3 g vanillin in 75 ml ethanol and 25 ml 85% phosphoric acid) and heated to 80° C. The antibiotic product of the formula (I) appears as a red spot. The developed tic plate can also be overlayed with agar seeded with either *S. aureus* or *B. subtilis* to which 2,3,5-triphenyl-2H-tetrazolium chloride monohydrate has been added and incubated at 37° C. for 16 hours to visualize the antibiotic (white spots against a pink background).

Scale-up in large fermentors was carried out by preparing shake flasks containing 0.7 liters of C' or JDYTT medium. The shake flask inoculum was fermented for 5 to 7 days at 28° C., and used to inoculate a 200 liter fermentation vessel containing 100 liters of UK1-2 medium. Approximately one liter of inoculum was used in the tank. The fermentation, after proceeding for 7 to 10 days, was harvested. The whole broth was extracted with ⅓ volume of methylisobutyl ketone at natural pH, separated on a DeLaval separator and the solvent concentrated in vacuo, initially on a cyclone still and finally in a rotating evaporator to yield crude antibiotic of the formula (I) as an oil, all of which was used in Example 2 below.

EXAMPLE 2

Isolation of the Antibiotic Compound of the Formula (I)

The entire crude product of the large scale fermentation of the preceding Example was chromatographed on 500 g of column grade silica gel slurried in hexane, and the column was eluted with ethyl acetate. The eluates were examined by thin-layer chromatography on silica gel plates developed with chloroform-isopropanol (95:5), then sprayed with 3.3% vanillin dissolved in ethanol-phosphoric acid (2:1). Upon heating to 80° C. the desired antibiotic of the formula (I) appeared as a red spot at Rf 0.30. Fractions containing the desired product were concentrated in vacuo, diluted up in ethyl acetate, treated with activated carbon and filtered. The filtered solvent was shaken first with phosphoric acid, then sodium phosphate dibasic buffer to form the sodium salt. After drying over sodium sulphate, the solvent was concentrated and the antibiotic crystallized upon the addition of heptane to afford 950 mg of a white solid. Further purification was accomplished by flash chromatography using a column of 100 g of silica gel, 32–63 microns, and employing a gradient of 95:5 to 50:50 chloroform-ethyl acetate. The product was eluted with 70:30 chloroform-ethyl acetate, and 852 mg of purified product was obtained following the removal of solvent under vacuum; m.p. 175°–177° C.; $[alpha]_D^{25}=+12.8°$ (c=1, methanol).

Anal. Calcd. for $C_{49}H_{83}O_{17}Na.H_2O$: C, 59.75; H, 8.67. Found: C, 59.47; H, 8.54.

C-13 nmr (chemical shift (ppm) in $CDCl_3$ with number of attached hydrogens in parentheses): 180.8(0), 106.7(0), 99.6 (0), 98.4(0), 96.6(1), 94.7(1), 88.8(1), 84.7(1), 83.4(1), 83.3(0), 80.3(0), 80.3(1), 80.3(1), 79.8(1), 79.3(1), 79.1(1), 74.3(1), 74.0(1), 67.5(1), 61.7(3), 61.6(1), 60.2(3), 59.9(3), 58.9(3), 56.8(3), 46.3(1), 46.1(1), 45.5(1), 40.7(1), 39.4(1), 36.9(1), 32.5(2), 31.9(2), 31.1(2), 29.2(2), 28.4(3), 27.7(2), 26.6(3), 25.6(2), 24.2(2), 23.0(2), 18.5(3), 13.1(3), 12.7(3), 12.5(3), 12.0(3), 11.5(3), 11.5(3) and 10.0(3).

The free acid form of antibiotic compound (I) was prepared by vigorously shaking a chloroform solution of the sodium salt with an equal volume of hydrochloric acid at pH 2 in a separatory funnel. The phases were separated and the chloroform layer was washed with water and then evaporated under vacuum to give the free acid; m.p. 95°–102° C.; $[alpha]_D^{25}=+20.2°$ (c=1, methanol);

Anal. Calcd. for $C_{49}H_{84}O_{17}.H_2O$: C, 61.10; H, 9.00. Found : C, 61.53; H, 9.31.

To reconvert to the sodium salt the free acid (from 2.6 g of the original sodium salt) was dissolved in 500 ml of chloroform. $Na_2CO_3$ (1 g) in 500 ml of $H_2O$ was added and the resulting mixture vigorously shaken in a separatory funnel for several minutes. The $H_2O$ layer was separated and washed with fresh chloroform. The combined organic phases were dried and evaporated under vacuum to afford 2.1 g of the sodium salt. The spectral properties and analytical data were identical with those found for the sodium salt obtained directly from fermentation as described above.

To prepare the rubidium salt of the antibiotic compound of the formula (I), the free acid (100 mg) was dissolved in 100 ml. of chloroform. Rubidium carbonate (150 mg in 100 ml of water) was added to the chloroform and the mixture was shaken vigorously in a separatory funnel for approximately 5 minutes. The organic phase was separated and extracted one time with water, and then evaporated to afford a white solid. The rubidium salt was recrystallized by slow evaporation from diethyl ether and the X-ray structure was determined on the resulting crystals by Dr. J. Bordner.

To prepare the potassium salt of the antibiotic compound of the formula (I), the free acid 229 mg was dissolved in 100 ml of chloroform. $K_2CO_3$ (75 mg) in 100 ml of $H_2O$ was added and the resulting mixture stirred for 15 minutes and was then placed in a separatory funnel and vigorously shaken for several minutes. The organic phase was separated and evaporated under vacuum to afford 224 mg of compound (I) as the potassium salt: m.p. 175°–179° C.; $[alpha]_D^{25}=+13.80°$ (c=1, methanol).

Anal. Calcd. for $C_{49}H_{83}O_{17}K.H_2O$: C, 58.78; H, 8.56. Found: C, 59.17; H, 8.89.

We claim:

1. A biologically pure culture of *Actinomadura sp.* ATCC 53676.

2. The culture of claim 1 in freeze-dried form.

* * * * *